United States Patent [19]

Lichtenberg

[11] Patent Number: 5,702,366
[45] Date of Patent: Dec. 30, 1997

[54] SAFETY FLUID COLLECTOR

[76] Inventor: Edward Lichtenberg, 2401 Pennsylvania Ave., Apt. 18 B27, Philadelphia, Pa. 19130

[21] Appl. No.: 775,950
[22] Filed: Jan. 3, 1997
[51] Int. Cl.$^6$ .............................. A61M 5/00
[52] U.S. Cl. ........................ 604/110; 128/763
[58] Field of Search ................. 604/110, 187, 604/240, 242, 243, 218, 272, 232; 128/765–767, 763, 764

[56] References Cited

U.S. PATENT DOCUMENTS

| 3,648,695 | 3/1972 | Bowen | 604/243 X |
| 4,950,253 | 8/1990 | Jacobs | 604/240 X |
| 5,120,311 | 6/1992 | Sagstetter et al. | 128/763 X |
| 5,201,716 | 4/1993 | Richard | 604/243 X |
| 5,246,423 | 9/1993 | Farkas | 604/110 |

Primary Examiner—John D. Yasko
Attorney, Agent, or Firm—Max Goldman

[57] ABSTRACT

A safety body fluid collector keeps a needle, held by a needle holder, in place frictionally with the use of an elastomeric O-ring. After use, the body fluid collector is inverted and placed over a discard container. Downward pressure on finger grips on the collector causes a tube of a disposal member, attached to the lid of the container, to press against the O-ring, unseating the O-ring and freeing the needle holder with the needle from the frictional hold of the O-ring. The needle holder and needle then drop into the discard container and when the discard container is full, it is discarded.

17 Claims, 3 Drawing Sheets 5,702,366

SAFETY FLUID COLLECTOR

BACKGROUND OF THE INVENTION

This invention relates generally to body fluid collectors and more specifically to a body fluid collector with a needle which can be safely and expeditiously removed for disposal.

In general, a basic problem exists in the handling of used needles by medical personnel to ensure that they are not inadvertently stuck or scratched by the needles. This can result in the transmission of viruses and other diseases.

One type of device has two coaxial tubes, one of which controls the movement of the needle with two sharpened ends. The needle is located in the center of the tubes. The control tube can be moved forward to its first position which extends the front end of the needle for use. The needle is frictionally held in position against a retracting spring force.

A vial is inserted into the open end of the tube and the rear end of the needle punctures a rubber-like diaphragm over the vial. The blood sample then flows into the vial through suction and when the vial is full, it is removed. Further motion of the control tube to a second position releases the frictional hold on the needle and the spring moves the needle back to its shielded position. A third position of the control tube locks the needle in that position. This device is complicated to manufacture and use and has, therefore, a relatively high cost.

Another commonly used type of safety fluid sampling device comprises an open-ended cylindrical member with one end threaded, a double-ended needle with a holder which can be screwed into the cylindrical threads and a separate container for used needles. Both ends of the needles are capped for protection prior to use. The rear end of the needle is uncapped and the needle assembly is screwed into the cylinder. The front end cap is then removed and an evacuation vial is inserted, filled and then removed. Several vials may then be filled.

A covered container is used to dispose of a plurality of used needles. Once a needle enters the disposal container, it is not easily withdrawn. In one design, the container cover has a shaped opening which grips the needle holder. Rotation of the cylinder unscrews the needle assembly which then drops into the container. This removal procedure has a disadvantage of requiring two hands and the needle must be stored while the medical technician is attending to the patient. Thus, there are chances for needle sticks and scratches and for reuse of the needle.

To obviate these problems, some container covers are equipped with a mechanism which grips and rotates the needle to unscrew it and then opens to allow the needle to drop into the container. Thus, the technician can dispose of the needle with one hand while still attending to the patient. Care must be used to operate the mechanism properly. When the container is full, a used needle may interfere with those in the container and the mechanism may jam or not operate properly. Moreover, there is no way the technician can tell whether the container is full. The need for threaded parts and a container mechanism are relatively costly.

In view of the foregoing, there is a need for a safety body fluid collector which is inexpensive, easy to manufacture and assemble and which assures safe and expeditious discarding of used needles and prevents reuse.

OBJECTS OF THE INVENTION

Accordingly, it is the general object of the instant invention to provide a safety body fluid collector which improves upon and overcomes the shortcomings of present devices.

It is a further object of the instant invention to provide a safety body fluid collector with a simple mechanism for releasing the needle holder with its needle from the collector for safe disposal.

It is yet a further object of the instant invention to provide a safety body fluid collector which allows for quick and efficient needle disposal after use with one hand, while the medical person or technician attends to the needs of the patient.

It is still yet a further object of the instant invention to provide a safety body fluid collector with a discard container which can store the needles in such a fashion that they cannot be removed prior to disposal.

It is another object of the instant invention to provide a safety body fluid collector which is inexpensive and simpler to manufacture, assemble and use than existing devices.

It is yet another object of the instant invention to provide a safety fluid collector for which used needles are separated from the remainder of the collector as they are disposed of.

It is still another object of the instant invention to provide a safety fluid collector which allows for disposal of used needles using one hand.

SUMMARY OF THE INVENTION

These and other objects of the instant invention are achieved by providing a safety body fluid collector with a discard container for the safe and efficient disposal of, and prevention of reuse of, used needles. The collector comprises a cylinder in which is placed a needle holder with a double-ended needle, upon which a bushing is slidingly fit. Prior to use, the front end of the needle and the rear end of the needle are capped. The needle is held in place frictionally by an elastomeric O-ring located between the inner wall of the cylinder and the outer surface of the needle holder. After use, the collector is placed over a tube extending from the lid of a discard container and the cylinder is pressed down by finger grips. This forces the O-ring out of its seat on the needle holder and onto the bushing. The needle holder, with its needle, is thereby released into the container. The disposal tube is transparent, allowing the medical technician or other personnel to determine when the container is full, so that it can be capped and disposed of.

DESCRIPTION OF THE DRAWINGS

Other objects and many of the intended advantages of this invention will be readily appreciated when the same becomes better understood by reference to the following detailed description, when considered in connection with the accompanying drawings, wherein.

DETAILED DESCRIPTION OF THE PREFERRED EMBODIMENT

Figure 1:
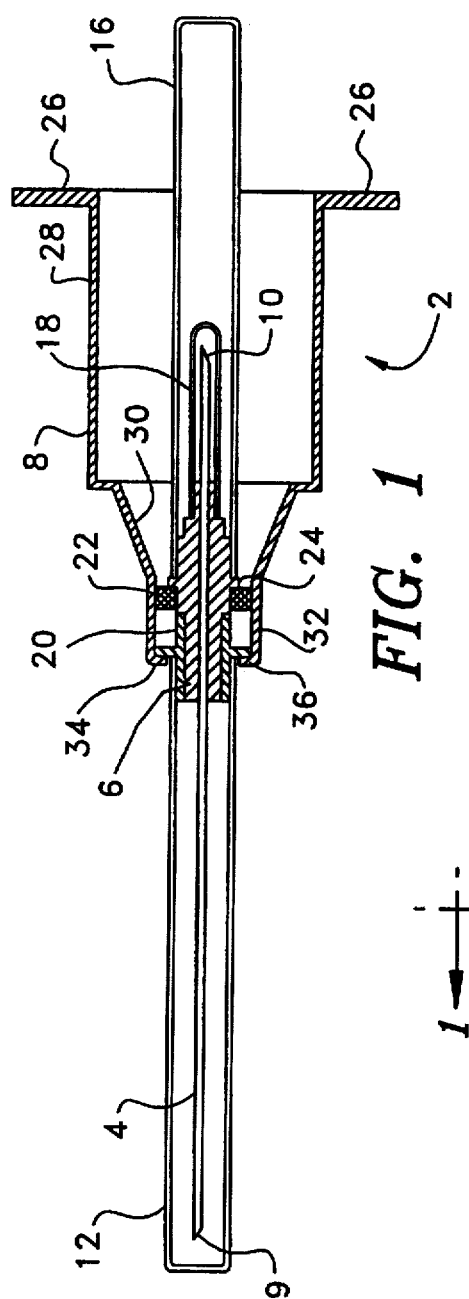
FIG. 1 is a side view, in section, of the body fluid collector of the instant invention.

Referring now in greater detail to the various figures of the drawings, wherein like reference characters refer to the parts, there is shown in FIG. 1 the body fluid collector 2 of the instant invention. The body fluid collector 2 comprises a double-ended needle 4 placed within a needle holder 6, which is positioned in a cylinder 8. The needle holder 4 has one sharp end 9 and a second sharp end 10, covered by caps 12 and 16, respectively. The collector 2 also comprises a bushing 20, which is slidingly fitted over the needle holder 6.

A sheath 18, comprising a rubber or rubber-like membrane, covers the needle end 10. The cylinder 8 comprises a cylindrical section 28, a tapered section 30 and an end section 32. An elastomeric O-ring 22 is positioned against the inner surface of the end section 32 and the outer surface of the needle holder 6. It is held in place by friction and is positioned during assembly against a ridge 24 on the outer surface of the needle holder 6. The end section 32 has a lip 34 which abuts a projecting section 36 of the bushing 20. The cylinder 8 also comprises finger grips 26 at its open end.

Figure 1B:
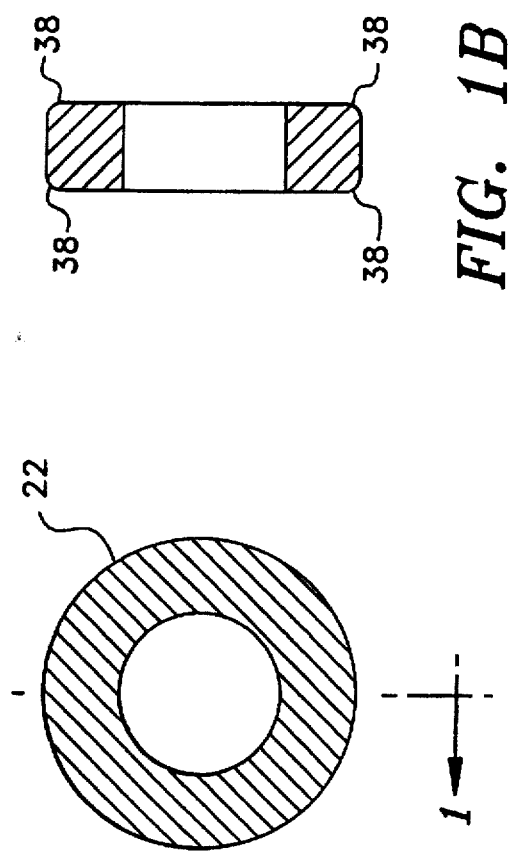
FIG. 1B is a sectional view of the O-ring taken along the line 1—1 of FIG. 1A.
Figure 1A:
FIG. 1A is an end view of the O-ring.

FIG. 1A shows an end view of the O-ring 22. As can be seen in FIG. 1B, the O-ring is square in cross section with slightly rounded outer corners 38.

The O-ring cross-section is made square to prevent rolling of the ring when it is moved out of position as will be explained later. Also, as will be explained later, the square cross section results in an increased frictional force to better hold the needle in position. The slight rounding of the corners of the O-ring assists in seating the O-ring during assembly of the body fluid collector 2.

Figure 2:
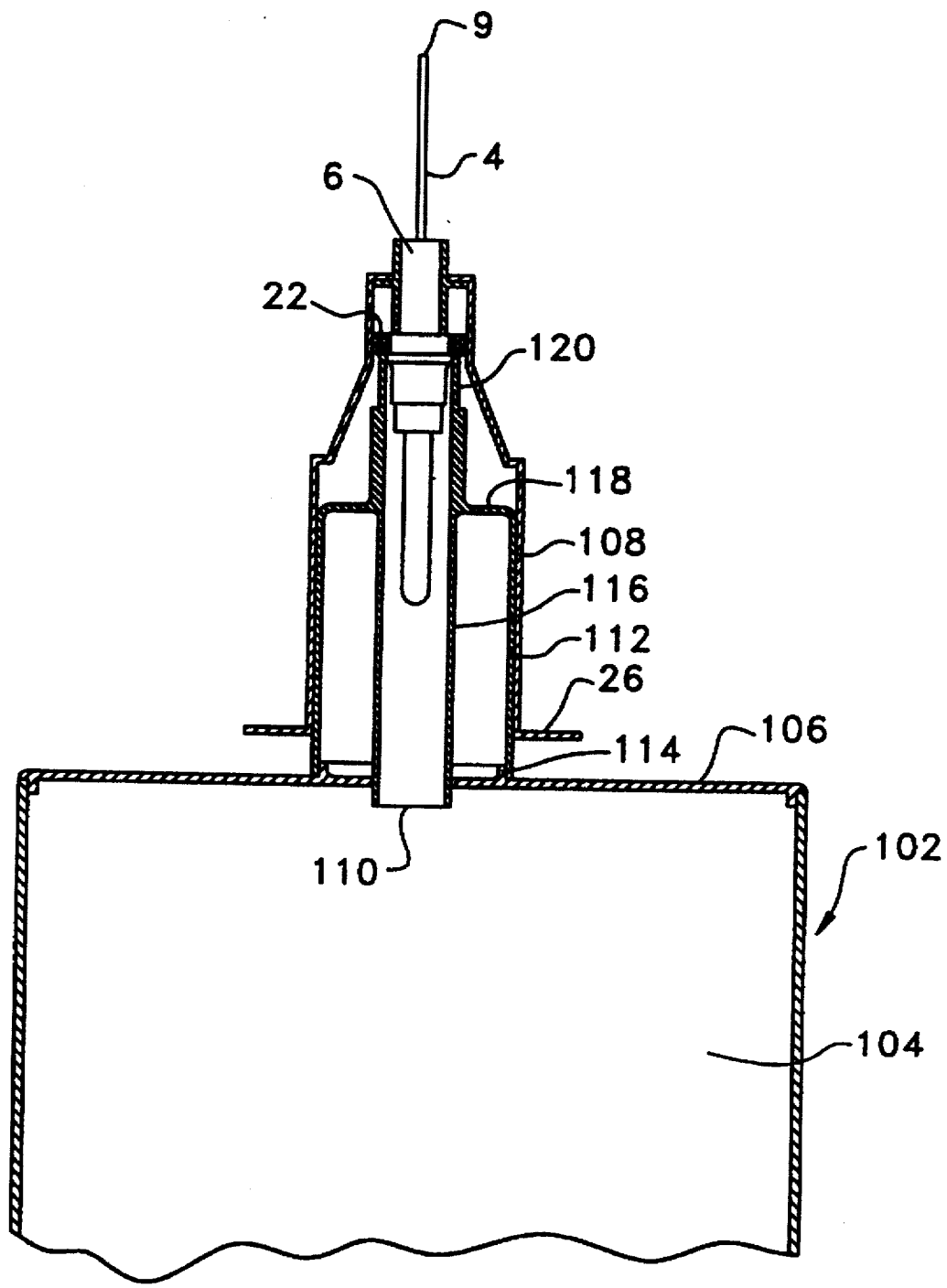
FIG. 2 is a side view in section of the body fluid collector in place atop the discard container prior to disposal of the needle.
Figure 3:
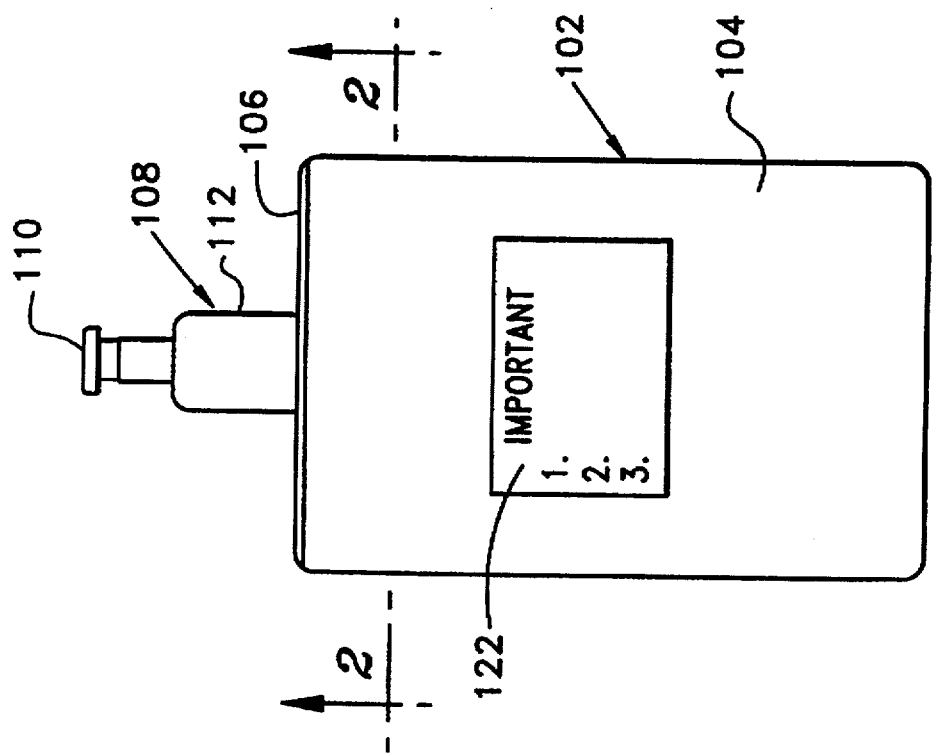
FIG. 3 is a side view of the disposal container.
Figure 3A:
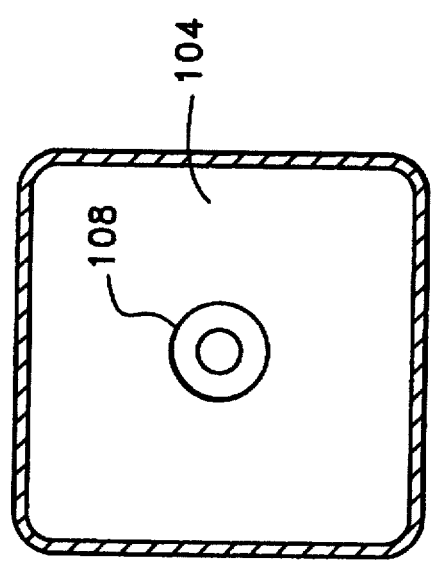
FIG. 3A is view of the container taken along the line 2—2 of FIG. 3.

The discard container 102 is shown in FIGS. 2 and 3. It comprises a body section 104, a lid 106 and a transparent disposal member 108 having a large diameter tube 112 and a coaxial, smaller diameter tube 116. The lid 106 has a circular lip 114 to which the large diameter tube 112 is attached. The tube 112 has a top portion 118 which is connected to the tube 116. The tube 116 also comprises an extending section 120 which is in contact with the O-ring 22 during needle disposal. The dispsal member also comprises a cap 110 to close the discard container 102 when it is not in use.

For needle disposal, when the body fluid collector 2 is inverted and placed over the tube 112, so that the finger grips 26 are adjacent to the lid 106, and downward pressure is placed on the finger grips 26, upward pressure against the O-ring 22 is applied, sliding the O-ring from its position on the needle holder 6 to a position on the bushing 20 outer surface and releasing the frictional hold on the needle holder 6. This frees the needle holder 6 causing the needle holder 6 with the needle 4 to slide from the bushing and drop into the discard container 102.

As can be seen in FIG. 3, a label 122 is placed on the discard container 102 providing a notice for the medical personnel disposing of needles. This instructs the person that the disposal tube must be empty and if not to call the supervisor. Further, after use, the medical person is to check that the needle has dropped to the disposal tube. And, finally, the medical person is instructed to snap on the safety cap after the needle has been deposited in the discard container.

A body fluid collector system has been described which allows for the safe and effective disposal of used needles and prevents reuse of used needles. The safety caps 12 and 16 are first removed from both ends of the needle 4. The distal end 9 of the needle is injected into the patient and a vial is placed through the opening in the cylinder down upon the needle end 10. This pierces the sheath 18 and fluids then flow into the vial because of the vacuum within the vial and the suction created thereby. After use, the vial is removed and the body fluid collector 2 is inverted with the finger grip 26 down and placed over the disposal tube 108. Further downward pressure on the finger grip 26 will cause the protruding section 120 of the inner wall 116 to press against the O-ring 22 to dislodge it from its seat. This releases the frictional hold of the O-ring against the needle holder 6 and the needle 4 and needle holder 6 is then free to drop into the discard container 102.

The use of the device is quite simple. The medical technician may use as many vials as required to collect as much body fluid as required. After use, the needle can be disposed of as described above, through the use of one hand by the medical technician, while the other hand is free to administer to the patient. Thus, the system prevents the reuse of needles and provides means for discard of a plurality of needles by use of the discard container.

The O-ring is made of an elastomeric material in order to provide a high coefficient of friction and to allow wide tolerances on the mating inside and outside diameters while closely controlling the induced radial pressure. The square section provides a large contact surface, which allows a large friction force for a given pressure. It also prevents rolling of the O-ring when large axial forces are applied to the needle in use.

Without further elaboration, the foregoing will so fully illustrate the invention, that others may, by applying current or future knowledge, readily adapt the same for use under the various conditions of service.

I claim:

1. A body fluid collector system comprising:
   (a) a needle holder with a needle;
   (b) a cylinder;
   (c) an O-ring seated within said cylinder and in contact with said needle holder to frictionally hold said needle holder, with said needle, in place when the fluid is extracted from the body;
   (d) a bushing slidingly fitted onto said needle holder;
   (e) means for releasing the frictional hold on said needle holder by said O-ring; and
   (f) a discard container for temporary storage of, and disposal of used needles.

2. The body fluid collector system of claim 1 wherein said needle comprises a first end for injection into the body and second end upon which a collecting vial is emplaced and wherein said body fluid collector system further comprises a removable first cap placed over said first end and a removable second cap placed over said second end for safety in transporting, storing and handling of said body fluid collector prior to use.

3. The body fluid collector system of claim 2 further comprising a sheath positioned over said second end.

4. The body fluid collector system of claim 3 wherein said needle holder further comprises a ridge against which said O-ring is seated.

5. The body fluid collector of claim 4 wherein said O-ring comprises aa elastomeric material and has a substantially square cross section with rounded outer corners.

6. The body fluid collector system of claim 5 wherein said cylinder comprises an end section with an end lip and said bushing comprises a protuberance which is in contact with said end lip.

7. The body fluid collector system of claim 6 wherein said cylinder comprises finger grips for the application of finger pressure to release said needle from said O-ring.

8. The body fluid collector system of claim 1 wherein said container comprises a body section, a lid, with an opening therein and a transparent disposal member positioned on said lid over said opening.

9. The body fluid collector system of claim 8 wherein said disposal member comprises a large diameter tube and a smaller diameter tube which projects past said large diameter tube, so that when said body fluid collector is placed over said disposal member and finger pressure is applied to said finger grips, said smaller diameter tube presses against said O-ring, dislodging said O-ring from its seat and onto said bushing and freeing said needle holder and needle to fall through said opening into said container.

10. The body fluid collector system of claim 9 wherein said disposal tube further comprises a cap for covering said disposal member when said container is full or when needles are not being discarded.

11. The body fluid collector system of claim 8 wherein said needle comprises a first end for injection into the body and second end upon which a collecting tube is emplaced and wherein said body fluid container system further comprises a removable first cap placed over said first end and a removable second cap placed over said second end for safety in transporting, storing and handling of said body fluid collector prior to use.

12. The body fluid collector system of claim 11 further comprising a collapsible sheath positioned over said second end.

13. The body fluid collector system of claim 12 wherein said needle holder further comprises a ridge against which said O-ring is seated.

14. The body fluid collector of claim 13 wherein said O-ring comprises an elastomeric material and has a substantially square cross section with rounded outer corners.

15. The body fluid collector system of claim 1 wherein said cylinder comprises an end section with an end lip and said bushing comprises a protuberance which is in contact with said end lip.

16. The body fluid collector of claim 15 wherein said cylinder comprises finger grips for the application of finger pressure to release said needle from said O-ring.

17. A body fluid collector comprising:
(a) a needle;
(b) a needle holder holding said needle;
(c) a cylinder,
(d) an O-ring set within said cylinder and in contact with said needle holder to frictionally hold said needle holder, with said needle, in place when the fluid is extracted from the body;
(e) means for releasing the frictional hold by said needle holder by said O-ring.

* * * * *